US00PP27568P2

(12) United States Plant Patent
Ludwig

(10) Patent No.: US PP27,568 P2
(45) Date of Patent: Jan. 17, 2017

(54) ***HEUCHERA* PLANT NAMED 'INHEUBRARA'**

(50) Latin Name: *Heuchera×hybrida*
Varietal Denomination: Inheubrara

(71) Applicant: Walter Ludwig, Heidesheim (DE)

(72) Inventor: Walter Ludwig, Heidesheim (DE)

(73) Assignee: Innovaplant Zierpflanzen GmbH & Co., KG, Gensingen (DE)

( * ) Notice: Subject to any disclaimer, the term of this patent is extended or adjusted under 35 U.S.C. 154(b) by 90 days.

(21) Appl. No.: 14/121,812

(22) Filed: Oct. 20, 2014

(51) Int. Cl.
*A01H 5/02* (2006.01)

(52) U.S. Cl.
USPC ..... Plt./440

(58) Field of Classification Search
USPC ..... Plt./440
See application file for complete search history.

(56) References Cited

PUBLICATIONS

Perennial Resource. *Heuchera* Dolce Brazen Raisin ('Inheubrara' PPAF CPBAF). retrieved on Mar. 16, 2016, retrieved from the Internet at <http://www.perennialresource.com/plants/general-perennial/2431_heuchera-dolce-reg-brazen-raisin-trade--inheubrara-ppaf-cpbraf.aspx> 3 pp.*

* cited by examiner

*Primary Examiner* — June Hwu
(74) *Attorney, Agent, or Firm* — C. A. Whealy

(57) ABSTRACT

A new and distinct cultivar of *Heuchera* plant named 'Inheubrara', characterized by its compact and uniformly mounded plant habit; vigorous growth habit; densely foliated and bushy appearance; very dark-colored leaves; numerous red purple-colored flower buds and flowers held above the foliar plane on dark purple-colored peduncles; and excellent garden performance.

1 Drawing Sheet

Botanical designation: *Heuchera×hybrida.*
Cultivar denomination: 'INHEUBRARA'.

BACKGROUND OF THE INVENTION

The present invention relates to a new and distinct *Heuchera* plant of *Heuchera*, botanically known as *Heuchera×hybrida* and hereinafter referred to by the name 'Inheubrara'.

The new *Heuchera* plant originated from an open-pollination during May, 2009 in Heidesheim, Germany of *Heuchera×hybrida* 'Fire Chief', disclosed in U.S. Plant Pat. No. 21,880, as the female, or seed, parent with an unknown selection of *Heuchera×hybrida* as the male, or pollen, parent. The new *Heuchera* plant was discovered and selected by the Inventor as a single flowering plant within the progeny of the stated open-pollination in a controlled greenhouse environment in Heidesheim, Germany in March, 2010.

Asexual reproduction of the new *Heuchera* plant by divisions in a controlled greenhouse environment in Gensingen, Germany since April, 2010 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inheubrara'. These characteristics in combination distinguish 'Inheubrara' as a new and distinct *Heuchera* plant:

1. Compact and uniformly mounded plant habit.
2. Vigorous growth habit.
3. Densely foliated and bushy appearance.
4. Very dark-colored leaves.
5. Numerous red purple-colored flower buds and flowers held above the foliar plane on dark purple-colored peduncles.
6. Excellent garden performance.

Plants of the new *Heuchera* differ from plants of the female parent, 'Fire Chief', in leaf color as plants of 'Fire Chief' have red to dark burgundy-colored leaves.

Plants of the new *Heuchera* can be compared to plants of the *Heuchera* 'Inheuredfu', disclosed in U.S. Plant Pat. No. 25,648. In side-by-side comparisons conducted in Gensingen, Germany, plants of the new *Heuchera* differed primarily from plants of 'Inheuredfu' in the following characteristics:

1. Leaves of plants of the new *Heuchera* were not ruffled whereas leaves of plants of 'Inheuredfu' were ruffled.
2. Plants of the new *Heuchera* and 'Inheuredfu' differed in leaf color.
3. Plants of the new *Heuchera* were more freely flowering than plants of 'Inheuredfu'.

Plants of the new *Heuchera* can also be compared to plants of the *Heuchera* 'Obsidian', disclosed in U.S. Plant Pat. No. 14,836. In side-by-side comparisons conducted in Gensingen, Germany, plants of the new *Heuchera* differed primarily from plants of 'Obsidian' in the following characteristics:

1. Plants of the new *Heuchera* were more vigorous than plants of 'Obsidian'.
2. Plants of the new *Heuchera* were more freely flowering than plants of 'Obsidian'.
3. Plants of the new *Heuchera* had larger flowers than plants of 'Obsidian'.
4. Plants of the new *Heuchera* had stronger flower peduncles than plants of 'Obsidian'.

BRIEF DESCRIPTION OF THE PHOTOGRAPH

The accompanying colored photograph illustrates the overall appearance of the new *Heuchera* plant showing the colors as true as it is reasonably possible to obtain in colored reproductions of this type. Colors in the photograph may differ slightly from the color values cited in the detailed botanical description which accurately describe the colors of the new *Heuchera* plant.

The photograph comprises a side perspective view of a typical plant of 'Inheubrara' grown in a ground bed.

DETAILED BOTANICAL DESCRIPTION

The aforementioned photograph and following observations, measurements and values describe plants grown during the early spring in two-gallon containers and ground beds in a polyethylene-covered greenhouse in Zeeland, Mich. and under cultural practices typical of commercial *Heuchera* production. During the production of the plants, day temperatures ranged from 15.5° C. to 19° C. and night temperatures ranged from 12.8° C. to 15° C. Plants were grown under long day/short night photoinductive conditions. Plants were two years old when the photograph and the description were taken. In the description, color references are made to The Royal Horticultural Society Colour Chart, 2007 Edition, except where general terms of ordinary dictionary significance are used.

Botanical classification: *Heuchera×hybrida* 'Inheubrara'.

Parentage:

*Female, or seed, parent.*—*Heuchera×hybrida* 'Fire Chief', disclosed in U.S. Plant Pat. No. 21,880.

*Male, or pollen, parent.*—Unknown selection of *Heuchera×hybrida*, not patented.

Propagation:

*Type.*—By tissue culture.

*Time to produce a rooted young plant, summer.*—About four to seven weeks at air temperatures ranging from 24° C. to 28° C.

*Time to produce a rooted young plant, winter.*—About five to eight weeks at air temperatures ranging from 18° C. to 21° C.

*Root description.*—Fine, fibrous; white in color.

*Rooting habit.*—Freely branching; medium density.

Plant description:

*Plant and growth habit.*—Herbaceous perennial; basal rosette plant habit with leaves developing from the base; densely foliated and dense and bushy appearance; compact and uniformly mounded plant habit; vigorous growth habit.

*Plant height, soil level to top of foliar plane.*—About 23 cm.

*Plant height, soil level to top of inflorescences.*—About 52 cm.

*Plant diameter or spread.*—About 44 cm.

Leaf description:

*Arrangement.*—Basal rosette, simple.

*Length.*—About 11.5 cm.

*Width.*—About 11.5 cm.

*Shape.*—Palmately-lobed.

*Apex.*—Rounded.

*Base.*—Cordate, frequently imbricate.

*Margin.*—Crenate with ciliation.

*Texture, upper surface.*—Sparsely pubescent; pubescence more prominent along veins.

*Texture, lower surface.*—Pubescent; pubescence more prominent along veins.

*Venation pattern.*—Palmate; reticulate.

*Color.*—Developing leaves, upper surface: Close to N186C. Developing leaves, lower surface: Close to 187B. Fully expanded leaves, upper surface: Close to N186A; venation, close to N186D; older leaves that are shaded becoming closer to between 147A and 139A. Fully expanded leaves, lower surface: Close to N186C; venation, close to 186A.

*Petioles.*—Length: About 11 cm. Diameter: About 2.2 mm. Texture, upper and lower surfaces: Pubescence. Color, upper and lower surfaces, developing leaves: Close to 187B. Color, upper and lower surfaces, fully expanded leaves: Close to 187A.

Flower description:

*Flower type and flowering habit.*—Single campanulate flowers arranged on erect panicles; each panicle with about 52 to 280 flowers and flower buds; flowers face mostly outward to slightly downward.

*Fragrance.*—None detected.

*Time of flowering.*—Plants flower continuously during the spring in Michigan.

*Inflorescence longevity.*—Individual flowers last about three days on the plant; flowers not persistent.

*Inflorescence length.*—About 52 cm.

*Inflorescence width.*—About 8 cm.

*Flower diameter.*—About 8 mm.

*Flower depth (height).*—About 8 mm.

*Flower buds.*—Height: About 7 mm. Diameter: About 2.5 mm. Shape: Elliptic; apex, acute. Color: Towards the base, close to 59C; towards the apex, close to 59D.

*Petals.*—Quantity and arrangement: Five petals in a single whorl. Length: About 4 mm. Width: About 1.5 mm. Shape: Spatulate. Apex: Acute. Margin: Entire. Texture, upper and lower surfaces: Smooth, glabrous. Color: When opening, upper and lower surfaces: Close to 155D. Fully opened, upper and lower surfaces: Close to 155D.

*Sepals.*—Quantity and arrangement: Five sepals in a single whorl; fused at base. Length: About 7 mm. Width: About 2.5 mm. Shape: Roughly lanceolate. Apex: Acute. Margin: Entire. Texture, upper and lower surfaces: Pubescent. Color: When developing and fully opened, upper surface: Towards the base, close to 56A; towards the apex, close to 56D. When developing and fully opened, lower surface: Towards the base, close to 59C; towards the apex, close to 59D.

*Peduncles.*—Length: About 52 cm. Diameter: About 3.5 mm to 4 mm. Strength: Strong. Aspect: Mostly erect. Texture: Pubescent. Color: Distally, close to 187A; proximally, close to 178A.

*Pedicels*.—Length: About 3.5 mm. Diameter: Less than 0.5 mm. Strength: Strong. Texture: Pubescent. Color: Close to 59A.

*Reproductive organs*.—Androecium: Stamen number: Five per flower. Filament length: About 3 mm. Filament color: Distally, close to 155D; proximally, close to 62D. Anther size: About 1 mm by 0.6 mm. Anther shape: Elliptic. Anther color: Close to 20A. Amount of pollen: Moderate. Pollen color: Close to 16B. Gynoecium: Pistil number: Two per flower. Pistil length: About 3 mm. Stigma shape: Globose. Stigma color: Close to 182C. Style length: About 3 mm. Style color: Distally, close to N155C; proximally, close to 62D. Ovary color: Close to 62D.

*Seeds*.—Length: About 1.5 mm. Diameter: Less than 0.5 mm. Color: Close to 202A.

Disease & pest resistance: Resistance to pathogens and pests has not been observed on plants of the new *Heuchera* grown under commercial conditions.

Garden performance: Plants of the new *Heuchera* have been observed to have excellent garden performance and to tolerate rain, wind and to be suitable for USDA Hardiness Zones 4 to 9.

It is claimed:

1. A new and distinct *Heuchera* plant named 'Inheubrara' as illustrated and described.

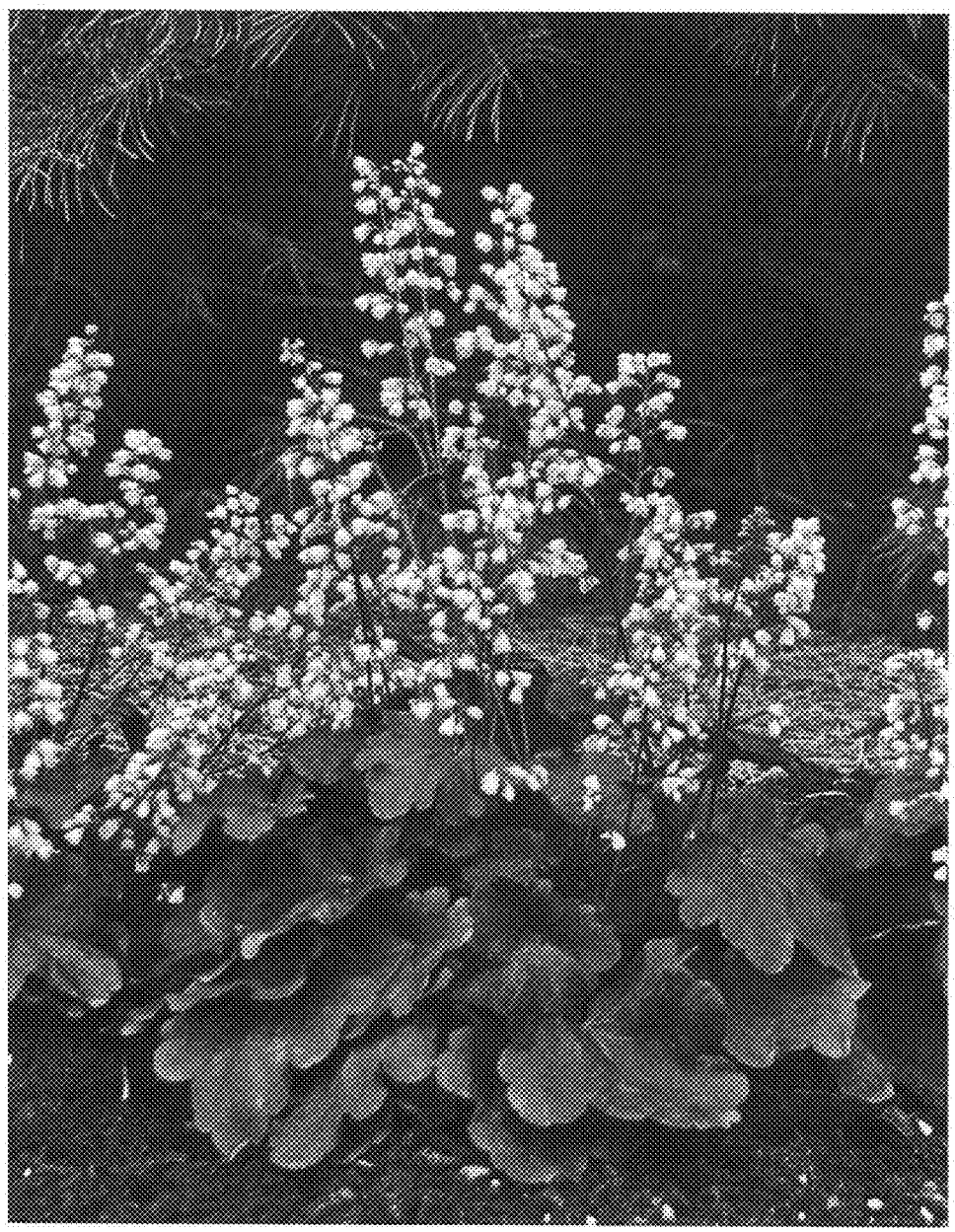

* * * * *